United States Patent
Christen

(10) Patent No.: US 6,524,629 B1
(45) Date of Patent: Feb. 25, 2003

(54) USE OF GINKGO BILOBA EXTRACTS FOR PREPARING A MEDICINE FOR TREATING AMYOTROPHIC LATERAL SCLEROSIS

(75) Inventor: Yves Christen, Paris (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/744,464
(22) PCT Filed: Aug. 6, 1999
(86) PCT No.: PCT/FR99/01948
§ 371 (c)(1), (2), (4) Date: Jan. 23, 2001
(87) PCT Pub. No.: WO00/07592
PCT Pub. Date: Feb. 17, 2000

(30) Foreign Application Priority Data

Aug. 7, 1998 (FR) .............................. 98 10187

(51) Int. Cl.$^7$ ................................................ A61K 35/78
(52) U.S. Cl. ........................................ 424/752; 424/725
(58) Field of Search .................................. 424/752, 725

(56) References Cited

PUBLICATIONS

XP–002100522 p. 302–307, C. Bruno et al. 1992.*
XP–002100523, p. 219–227, S. Brailowsky et al. 1996.*
XP–002100522 p. 302–307, C. Bruno et al 1992.
XP–002100523 p. 219–227, S. Brailowsky et al 1996.
XP 002008240, p. 64–72, J.L. Seeburger et al, 1993.
XP 002008239, p. 752–757, O. Lindvall et al, 1994.
XP–002100524, p. 141–146, P. Guinot et al, 1994.

* cited by examiner

Primary Examiner—Christopher R. Tate
Assistant Examiner—Randall Winston
(74) Attorney, Agent, or Firm—Bierman, Muserlian and Lucas

(57) ABSTRACT

The invention relates to the use of extracts of *Ginkgo biloba*, and in particular extracts of *Ginkgo biloba* comprising 20 to 30% of flavoneglycosides, 2.5 to 4.5% of ginkgolides A, B, C and J, 2 to 4% of bilobalide, less than 10% of proanthocyanidines and less than 10 ppm of compounds of alkylphenol type, for preparing a medicament intended to treat amyotrophic lateral sclerosis.

3 Claims, No Drawings

USE OF GINKGO BILOBA EXTRACTS FOR PREPARING A MEDICINE FOR TREATING AMYOTROPHIC LATERAL SCLEROSIS

The invention relates to the use of extracts of *Ginkgo biloba* for preparing a medicament intended to treat amyotrophic lateral sclerosis (ALS).

It is already known that extracts of *Ginkgo biloba* have an activity in the cardiovascular field (in particular the reduction of platelet adhesion), in the central nervous field (in particular a neuroprotective activity) or in the neurosensory system (in particular retinal protection); cf. for example DeFeudis et al., *Ginkgo Biloba* Extract (EGb 761), Pharmaceutical Activities and Clinical Applications (Elsevier, Paris, 1991). Their preparation has been the subject of a certain number of patents, of which there can be mentioned the European Patents EP 431 535 and EP 431 536, and the American Patent U.S. Pat. No. 5,389,370.

Certain products can be used in the treatment of ALS. In particular there can be mentioned riluzole, gabapentin, 1-(2-naphth-2-ylethyl)-4-(3-trifluoromethylphenyl)-1,2,3,6-tetrahydropyridine or vitamin E (cf. Gurney M. E. et al., *Ann. Neurol.*, 39 (1996), 147–157; Patent Application PCT WO 97/15304).

Now the Applicant has just found that certain extracts of *Ginkgo biloba* also have useful new pharmacological properties, namely retarding and attenuating the symptoms of ALS. In particular, the Applicant was able to note the beneficial effects of these extracts on genetically modified mice suffering from ALS.

Therefore a subject of the invention is the use of these extracts for preparing a medicament intended to treat ALS.

By extract of *Ginkgo biloba* is understood at least one of the individual compounds which can be obtained by extraction from the *Ginkgo biloba* L. tree, and in particular a flavonoid compound or a terpene such as a ginkgolide or a bilobalide, or also a mixture of the latter. Preferably, the extract used will be such that it contains an effective quantity of ginkgolides. For the uses according to the invention, an extract of type EGb 761 or CP 401 can for example be chosen.

By ginkgolide is understood all the natural ginkgolides obtained from the *Ginkgo biloba* tree, as well as synthetic ginkgolides and their derivatives (resulting for example from an acetylation or alkoxylation reaction) and pharmaceutically active salts. The ginkgolides used can for example be ginkgolide A, ginkgolide B, ginkgolide C, ginkgolide J or ginkgolide M (structures given in the diagram below; these compounds can be isolated from extracts of *Ginkgo biloba* leaves—see GINKGOLIDES, Chemistry, Biology, Pharmacology and Clinical Perspectives, published by P. Braquet, J. R. Prous Science Publishers, in particular Volumes 1 (1988) and 2 (1989)). Glycosylated derivatives of ginkgolides or alkoxylated or acetylated derivatives of ginkgolides can also be used (cf. Weber, M. and Vasella, A., *Helv. Chim. Acta*, 80 (1997) 2352–2367). By alkoxylated derivative of ginkgolide is understood a ginkgolide derivative comprising at least one linear or branched alkoxy group, instead of a hydroxy group (these compounds are described in French Patent Application No. FR 88.14392). Similarly, by acetylated derivative of ginkgolide is understood a derivative of ginkgolide comprising at least one acetate group instead of a hydroxy group.

Structure of ginkgolides A, B C, J and M

| Ginkgolide | W | X | Y | Z |
|---|---|---|---|---|
| A | OH | OH | H | H |
| B | OH | OH | OH | H |
| C | OH | OH | OH | OH |
| J | OH | OH | H | OH |
| M | H | OH | OH | OH |

By extract of type EGb 761 is understood an extract of a composition substantially identical to that of the standardized extract EGb 761 as defined in particular in the following article: K. Drieu, La presse medicale, 31, Sep. 25, 1986, supplement devoted to the extract of *Ginkgo biloba* (EGb 761), 1455–1457; or in the European Patents EP 431 535 and EP 431 536; by extract of type EGb 761 is therefore understood in particular extracts of *Ginkgo biloba* comprising 20 to 30% of flavoneglycosides, 2.5 to 4.5% of ginkgolides A, B, C and J, 2 to 4% of bilobalide, less than 10% of proanthocyanidines and less than 10 ppm, and preferably less than 5 ppm, of compounds of alkylphenol type, and in particular extracts of *Ginkgo biloba* comprising approximately 24% of flavoneglycosides, 3.1% of ginkgolides A, B, C and J, 2.9% of bilobalide, 6.5% of proanthocyanidines and less than 1 ppm of compounds of alkylphenol type. By extract of type CP 401 is understood extracts such as those which are presented in the U.S. Pat. No. 5,389,370, in particular extracts of *Ginkgo biloba* containing 5.5 to 8% of ginkgolides A, B, C and J, 40 to 60% of flavoneglycosides and 5 to 7% of bilobalide, and quite particularly extracts containing approximately 7% of ginkgolides A, B, C and J, 50% of flavoneglycosides and 6% of bilobalide.

The invention also relates to the use of a compound of general formula (I)

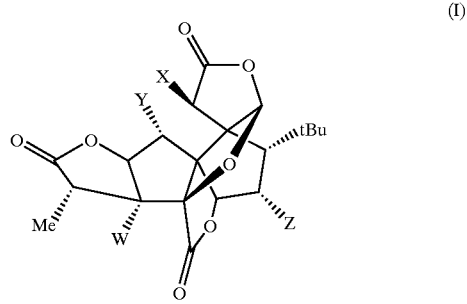

(I)

in which W, X, Y and Z represent independently the H, OH, linear or branched alkoxy or O-$G_S$ radicals, $G_S$-OH representing a mono- or a disaccharide, or one of their derivatives or analogues, it being understood that at least one of W, X, Y or Z represents an O-$G_S$ radical, for preparing a medicament intended to treat ALS.

The invention preferably relates to the use of a compound of general formula (I)

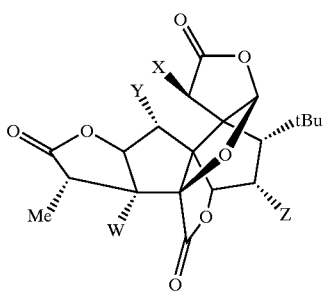

in which X represents an OH or O-G$_S$ radical, G$_S$-OH representing a mono- or a disaccharide, or one of their derivatives or analogues, and:
either W represents an OH or O-G$_S$ radical, Y represents H and Z represents H;
or W represents an OH or O-G$_S$ radical, Y represents an OH or O-G$_S$ radical and Z represents H;
or W represents an OH or O-G$_S$ radical, Y represents an OH or O-G$_S$ radical and Z represents an OH or O-G$_S$ radical;
or W represents an OH or O-G$_S$ radical, Y represents H and Z represents an OH or O-G$_S$ radical;
or W represents H, Y represents an OH or O-G$_S$ radical and Z represents an OH or O-G$_S$ radical;
or W represents an OH or O-G$_S$ radical, Y represents a linear or branched alkoxy radical and Z represents H;
it being understood that at least one of W, X, Y or Z represents an O-G$_S$ radical, for preparing a medicament intended to treat ALS.

The invention quite particularly relates to the use of a compound of general formula (I)

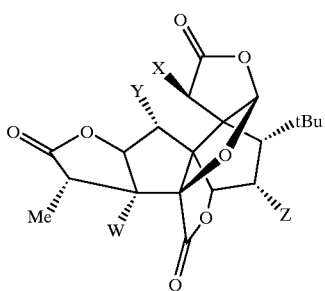

in which X represents an OH or O-G$_S$ radical, G$_S$-OH representing a mono- or a disaccharide, or one of their derivatives or analogues, and:
either W represents an OH or O-G$_S$ radical, Y represents H and Z represents H;
or W represents an OH or O-G$_S$ radical, Y represents an OH or O-G$_S$ radical and Z represents H;
or W represents an OH or O-G$_S$ radical, Y represents a linear or branched alkoxy radical and Z represents H;
it being understood that at least one of W, X, Y or Z represents an O-G$_S$ radical, for preparing a medicament intended to treat ALS.

By linear or branched alkoxy radical, is understood in the present description an alkoxy radical the linear or branched carbon-containing chain of which, contains 1 to 6 carbon atoms. By derivative or analogue of mono- or disaccharides, is understood compounds such as N-acetylglucosamine, N-acetylalosamine, galactosamine, mannoseamine, N-tosylhydrazone, etc.

Preferably, O-G$_S$ will be chosen so that G$_S$-OH belongs to the group comprising abequose, rhamnose, arabinose, ribose, xylose, 2-deoxyribose, glucose, galactose, mannose, 2-deoxyglucose, fructose, fucose, N-acetylglucosamine, N-acetylalosamine, galactosamine, mannosamine, saccharose, lactose, maltose, cellobiose and trehalose. Yet more preferably, O-G$_S$ will be chosen so that G$_S$-OH belongs to the group comprising glucose and lactose.

The different processes for obtaining the glycolsylated derivatives of ginkgolides or alkoxylated ginkgolides (i.e. those resulting from a glycosylation reaction carried out on at least one of the OH groups of the ginkgolides or of their alkoxylated derivatives) are described in the following publication: Weber, M. and Vasella, A., *Helv. Chim. Acta,* 80 (1997), 2352–2367.

According to a variant of the invention, the ginkgo extract can also be combined with at least one of the following compounds: riluzole, gabapentin, creatine, 1-(2-naphth-2-ylethyl)-4-(3-trifluoromethylphenyl)-1,2,3,6-tetrahydropyridine (also known under the code name SR-57746 A) or its pharmaceutically acceptable salts, or also a compound having an action on the N-methyl-D-aspartate (NMDA) receptors and the metabolism of glutamate, in particular dizocilpine or arylcyclohexylamines such as gacyclidine (or cis-2-methyl-1-(1-piperidinyl)-1-(2-thienyl)cyclohexane), phencyclidine and ketamine (or also those as defined in the Patent EP 396734). The invention therefore relates to a product comprising at least one extract of ginkgo in combination with at least one compound chosen from the group comprising riluzole, gabapentin, creatine, 1-(2-naphth-2-ylethyl)-4-(3-trifluoromethylphenyl)-1,2,3,6-tetrahydropyridine (also known under the code name SR-57746 A) or its pharmaceutically acceptable salts, or also a compound having an action on the N-methyl-D-aspartate (NMDA) receptors and the metabolism of glutamate, in particular gacyclidine, dizocilpine or arylcyclohexylamines such as phencyclidine and ketamine (or also those as defined in the Patent EP 396734), for a therapeutic use which is simultaneous, separate or spread out over time, in the treatment of ALS. Preferably, at least one extract of ginkgo will be combined with riluzole or at least one extract of ginkgo with 1-(2-naphth-2-ylethyl)-4-(3-trifluoromethylphenyl)-1,2,3,6-tetrahydropyridine. Particularly preferably, at least one extract of ginkgo will be combined with riluzole and 1-(2-naphth-2-ylethyl)-4-(3-trifluoromethylphenyl)-1,2,3,6-tetrahydropyridine. Optionally, all the products mentioned previously can also contain vitamin E.

By simultaneous therapeutic use, is understood in the present Application an administration of several active ingredients by the same route and at the same time. By separate use, is understood in particular an administration of several active ingredients approximately at same time by different routes. By therapeutic use spread out over time, is understood an administration of several active ingredients at different times and in particular an administration method according to which all of the administration of one of the active ingredients is carried out before the administration of the other or others commences. One of the active ingredients can therefore be administered several months before administration of the other active ingredient or ingredients. There is no simultaneous treatment in this case.

The pharmaceutical compositions comprising a compound of the invention can be in the form of solids, for example powders, granules, tablets, capsules, liposomes or suppositories. Appropriate solid supports can be for example calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in the form of a liquid, for example, solutions, emulsions, suspensions or syrups. Appropriate liquid supports can be, for example, water, organic solvents such as glycerol or the glycols, as well as their mixtures, in varying proportions, in water.

The administration of a medicament according to the invention can be done by topical, oral, parenteral route, by injection (intramuscular, subcutaneous, intravenous, etc), etc.

The daily administration dose envisaged for the active ingredients which can be used according to the invention is comprised between 0.1 mg to 10 g depending on the type of active ingredient and the gravity of the ALS of the patient to be treated. Preferably, for the extracts of *Ginkgo biloba*, a dose comprised between 20 and 200 mg per day approximately will be chosen. For riluzole, the preferred dose will be of the order of 50 to 150 mg per day approximately, and for gabapentin, of the order of 500 to 3000 mg per day approximately. As regards 1-(2-naphth-2-ylethyl)-4-(3-trifluoromethylphenyl)-1,2,3,6-tetrahydropyridine, the preferred dose will be comprised between 1 to 5 mg per day approximately, and preferably comprised between 1 and 3 mg per day. Finally, vitamin E will be preferably administred at a dose of 100 to 500 mg per day approximately.

Unless they are defined in another manner, all the technical and scientific terms used here have the same meaning as that commonly understood by an ordinary specialist in the field to which this invention belongs. Similarly, all publications, patent applications, all patents and other references mentioned here are incorporated by way of reference.

In order to show the importance of the use of extracts of ginkgo in the treatment of ALS, the following tests were carried out:

Pharmacological Part

Description of the Tests

For the two tests which follow, the mice were divided into three groups of 12:

the first group receives a normal diet only;

the second receives a dose of 50 mg/kg/day of EGb 761 with its diet; and the third receives a dose of 100 mg/kg/jour of EGb 761 with its diet.

1) Survival and Motor Performances

For this test, the motor behaviour of the animals is observed. Every day, the following test is carried out: the mice are placed on their side, and those which are incapable of getting up in 10 seconds are sacrificed. Their life span is then compared to the life span of the control group which is approximately 145 days on average.

2) "Rotarod" Test

For this test, the mice are placed in a treadmill with rods on which they can cling. The Rotarod is turned at a speed of 1 rev/min, then every 10 seconds this speed is increased by 1 rev/min each time, until the mouse falls. After three tests, the speed at which the mouse falls is noted. The mice are tested every two days starting from day 100.

In order to obtain reproducible results, the mice are given two days to understand the process before results are taken. The test is stopped when the mice can no longer hold on even at a speed of rotation of 1 rev/min.

Mice Used

For the two tests, genetically modified mice G93A are used as described in particular in the following publications: Gurney M. E. et al., *Ann. Neurol.,* 39 (1996), 147–157; and Gurney M. E. et al., *Science,* 264 (1994), 1772–1775. The mice used are 50 to 60 days old at the start of the first test, and 100 days at the start of the second.

What is claimed is:

1. A method of treating amyotrophic lateral sclerosis in a human being comprising administering to said human an amount of an extract of *Ginkgo biloba* comprising 20 to 30% of flavoneglycosides, 2.5 to 4.5% of ginkgolides A, B, C and J, 2 to 4% of bilobalide, less than 10% of proanthocyanidines and less than 10 ppm of compounds of alkylphenol type, all being by weight.

2. The method of claim 1 wherein the extract of *Ginkgo biloba* is containing 5.5 to 8% of ginkgolides A, B, C and J, 40 to 60% of flavoneglycosides and 5 to 7% of bilobalide, all percentages being by weight.

3. The method of claim 2 wherein the extract of Ginkgo biloba contains less than 5 ppm of compounds of alkylphenol type by weight.

* * * * *